United States Patent [19]

Warriner

[11] Patent Number: Plant 6,317

[45] Date of Patent: Oct. 4, 1988

[54] ROSE PLANT JACHAD

[75] Inventor: William A. Warriner, Tustin, Calif.

[73] Assignee: Jackson & Perkins Company, Medford, Oreg.

[21] Appl. No.: 936,010

[22] Filed: Nov. 28, 1986

[51] Int. Cl.[4] ..... A01H 5/00

[52] U.S. Cl. ..... Plt./11

[58] Field of Search ..... Plt./11

*Primary Examiner*—James R. Feyrer

*Attorney, Agent, or Firm*—Majestic, Gallagher, Parsons & Siebert

[57] ABSTRACT

A hybrid tea rose variety having upright, vigorous growth, dark green foliage, orange and yellow blend flowers, powdery mildew resistance, profusion of small prickles on stems and large, sweet-tasting orange-colored hips.

1 Drawing Sheet

This present invention relates to a new and distinct variety of rose plant of the hybrid tea class which was originated by crossing an unnamed variety with the variety Sunshine, U.S. Plant Pat. No. 3,791.

The primary objective of this breeding was to produce a new rose variety of the hybrid tea class exhibiting a rich blend of yellow and orange combined with good growth habits. This objective was substantially achieved along with other desirable improvements as evidenced by the following unique combination of characteristics which are outstanding in the new variety and which distinguish it from its parents as well as from all other varieties of which I am aware:

1. An unusual blend of yellow and orange color;
2. Upright vigorous growth;
3. Powdery mildew resistance;
4. Stems covered with small prickles;
5. Dark green foliage; and
6. Large orange-colored hips.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Unnamed variety.

*Pollen parent.*—Sunshine, U.S. Plant Pat. No. 3,791.

Classification:

*Botanical.*—Rosa hybrid.

*Commercial.*—Hybrid tea.

FLOWER

Observations made from specimens grown in a greenhouse at Irvine, Calif. in September–October, 1986.

Blooming habit: Continuous.

Bud:

*Size.*—1½" when petals start to unfurl.

*Form.*—Long, pointed ovoid.

*Color.*—When sepals first divide, the base of the bud is Yellow Group 8A changing to 8B halfway up the bud before turning to orange-red at the tips of the bud (Orange-Red 34B to C); when half blown, upper side of petals a blend of colors beginning with an underlay of Orange-Yellow Group 17B with an overlay, especially at the petal margins and the outer petals of Orange-Red 34A to B; lower side of petals, the petal bases are Yellow Group 8A to B fading to 8C halfway up the petal; the petal edges on the underside are edged in Orange-Red 34B.

*Sepals.*—Color: Green Group 138B. Three appendaged sepals lightly appendaged. Two unappendaged sepals hairy edged.

*Receptacle.*—Color: Green Group 138B. Shape: Funnel. Size: Normal. Surface: Smooth.

*Peduncle.*—Length: Medium. Surface: Prickly. Color: Bronzy. Strength: Stiff.

Open bloom:

*Size.*—Large. Average open size 5".

*Borne.*—Singly.

*Stems.*—Medium.

*Form.*—When first open, high center. Permanence: Retains its form to the end, outer petals curl back quill fashion.

*Petalage.*—Number of petals under normal conditions; 30–35.

*Color.*—Center of flower: Upper side of petals, Orange-Yellow Group 17B with an overlay, especially at the petal fringe and on the outside petals of Orange-Red Group 34A to B; reverse side of petals, dominated by Yellow Group 8A to B fading to 8C halfway up the petals. On the outer fringe of the petal is color group Orange-Red 34B. Base of petals, Yellow Group 8A. Major color: Orange-Yellow Group 17B on the upper and Yellow Group 8B on the lower side of the petals.

*Discoloration.*—General tonality at end of first day: None. Third day: None to a slight fading if growing conditions are hot and sunny.

*Fragrance.*—Slight to moderate.

Petals:

*Texture.*—Thick.

*Shape.*—Round.

*Form.*—Tips slightly recurved.
*Arrangement.*—Imbricated. Petaloids in center, few.
*Persistence.*—Drop off cleanly.
*Lastingness.*—On the plant, long. As cut flower, long.

Reproductive parts:
*Anthers.*—Medium. Color: Yellow. Arrangement: Regular around styles and mixed with petaloids.
*Filaments.*—Color: Yellow.
*Pollen.*—Gold Yellow.
*Styles.*—Color: Red.
*Stigmas.*—Color: Greenish white. Hips are 1 to 1½" in diameter, bright orange at maturity and contain 5 to 10 seed. Walls of the hip are thick averaging ¼" of bright orange sweet flesh.

PLANT

Form: Bush.
Growth: Vigorous, upright.
Foliage: Number of leaflets on normal mid-stem leaves: 5 with occasional 7.
*Size.*—Medium.
*Quantity.*—Normal.
*Color.*—New foliage: Reddish. Old foliage: Dark green.

Leaflets:
*Shape.*—Elliptic.
*Texture.*—Leathery, smooth.

*Edge.*—Serrated.
*Serration.*—Single.
*Petiole.*—Rachis: Color: Green. Underside: Rough with prickles.
*Stipules.*—Medium, bearded.
*Disease resistance.*—Resistant to mildew, under normal growing conditions at Irvine, Calif.

Wood:
*New wood.*—Color: Reddish. Bark: Smooth.
*Old wood.*—Color: Green. Bark: Smooth.

Prickles:
*Quantity.*—On main canes from base: Ordinary. On laterals from main canes: Ordinary.
*Form.*—Medium, hooked downward.
*Color when young.*—Red.

Small prickles:
*Quantity.*—On main stalks, many. On laterals, many.
*Color.*—Brown.

I claim:

1. A new and distinct variety of rose plant of the hybrid tea class, substantially as herein shown and described, characterized particularly as to novelty by the unique combination of its upright, vigorous growth, dark green foliage, orange and yellow blend flowers, powdery mildew resistance, profusion of small prickles on stems and large, sweet-tasting orange-colored hips.

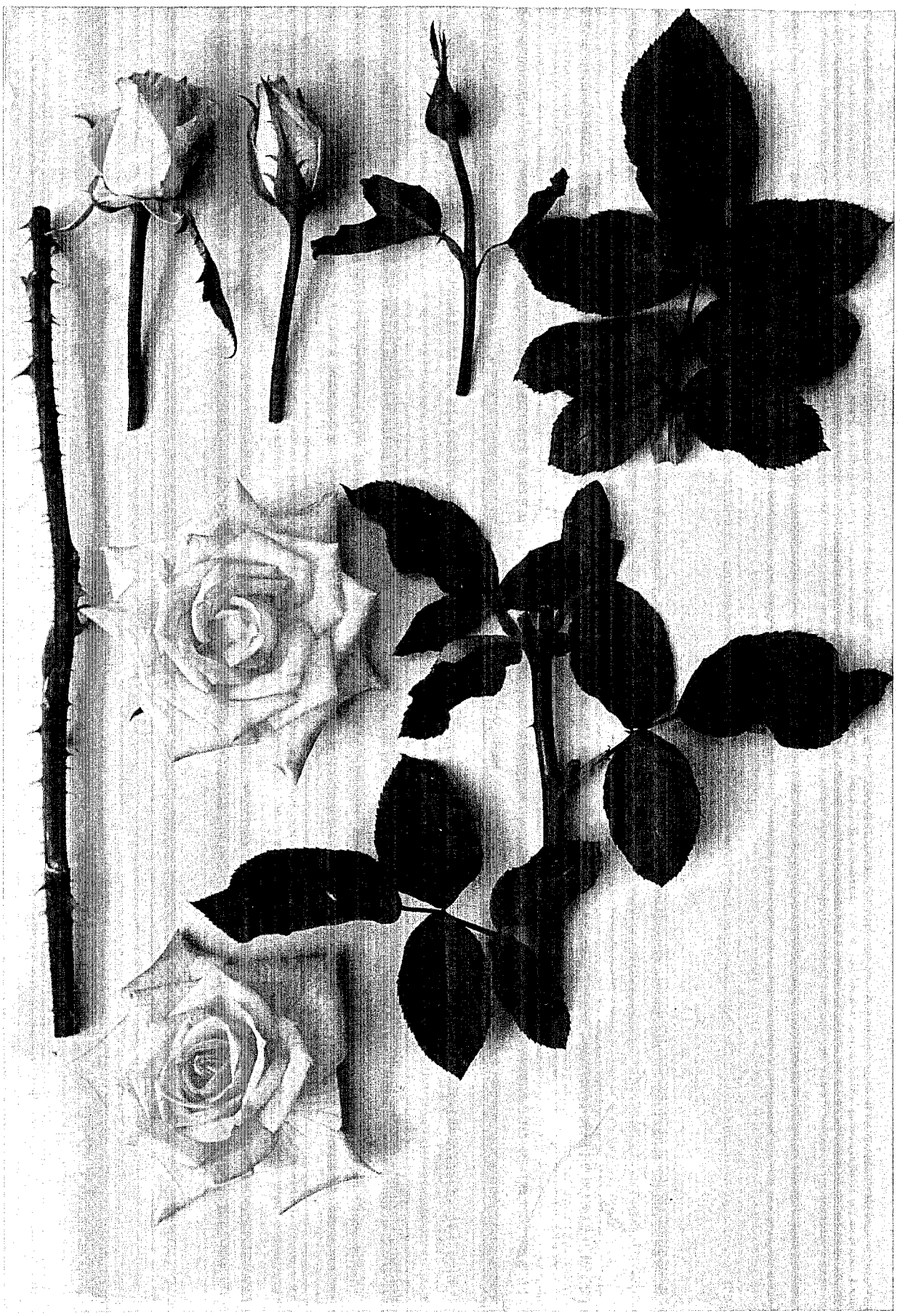

* * * * *